United States Patent
Comrie et al.

(10) Patent No.: US 7,087,015 B1
(45) Date of Patent: Aug. 8, 2006

(54) NEUROLOGICAL PATHOLOGY DIAGNOSTIC APPARATUS AND METHODS

(75) Inventors: McDonald Comrie, Staten Island, NY (US); David Michael Erlanger, New York, NY (US); Darin F Kaplan, New York, NY (US); Vladislav Shchogolev, Brooklyn, NY (US); Alexis Theodoracopulos, New York, NY (US); Philip Yee, New York, NY (US)

(73) Assignee: PanMedix, Inc., New York, NY (US)

( * ) Notice: Subject to any disclaimer, the term of this patent is extended or adjusted under 35 U.S.C. 154(b) by 0 days.

(21) Appl. No.: 09/494,475

(22) Filed: Jan. 31, 2000

(51) Int. Cl.
*A61B 5/00* (2006.01)

(52) U.S. Cl. .................. 600/300; 434/236; 128/904
(58) Field of Classification Search ............... 600/300, 600/301, 544, 545; 128/900, 903–905, 920–925; 705/2–4; 434/262, 236–238
See application file for complete search history.

(56) References Cited

U.S. PATENT DOCUMENTS

| | | | | |
|---|---|---|---|---|
| 4,770,636 | A | * | 9/1988 | Bushke .................. 434/236 |
| 5,832,488 | A | * | 11/1998 | Eberhardt ................ 707/10 |
| 5,911,581 | A | * | 6/1999 | Reynolds et al. ........... 434/236 |
| 6,113,538 | A | * | 9/2000 | Bowles et al. ............. 600/300 |
| 6,241,686 | B1 | * | 6/2001 | Balkin et al. ............. 600/544 |
| 6,245,014 | B1 | * | 6/2001 | Brainard, II ............. 600/595 |
| 6,280,198 | B1 | * | 8/2001 | Calhoun et al. ........... 434/236 |

OTHER PUBLICATIONS

Hinton–Bayre et al., Concussion in Contact Sports: Reliable Change Indices of Impairment and Recovery, 1999, Journal of Clinical and Experimental Neuropsychology, vol. No. 1, pp. 77–86.*
Michael W. Collins et al., "Current Issues In Managing Sports–Related Concussion," 282 JAMA 2283 (1999).
Michael W. Collins et al., "Relationship Between Concussion and Neuropsychological Performance," 282 JAMA 964 (1999).
Erik J.T. Matser et al., "Neuropsychological Impairment In Amateur Soccer Players," 282 JAMA 971 (1999).
M. Mrazik et al., "Neuropsychological Assessment Of College Football Players," (publication title and date unavailable).
Joseph Bleiberg et al., "Factor Analysis Of Computerized and Traditional Tests," 14 Clin. Neuropsychol. 295 (2000).
Ruben J. Echemendia et al., "Neuropsychological Evaluation of Mild Traumatic Brain Injury In Sports," National Acad. of Neuropsychology, Inc. Course No. 42 (date unvailable).

Ruben J. Echemendia et al., "Mild Traumatic Brain Injury In Sports: Neuropsychology's Contribution to a Developing Field," (undated, pre–publication draft).
David Erlanger et al., "Neuropsychological Test Performance Prior To and Following Sports Related Mild Traumatic Brain Injury," (undated pre–publication draft).
David M. Erlanger et al., "Neourpsychology of Sprots–Related Head Injury," 13 Clin. Neuropsychol. 193 (1999).
Robert C. Cantu, "Head Injuries In Sport," (publication title and date unavailable).
David Maddocks et al., "Neuropsychological Deficits Following Concussion," 10 Brain Injury 99 (1996).
Kenneth C. Kutner et al., "Computerized Neuropsychological Assessment In the NFL," NFL Physician Society Science Symposium (Feb. 7, 1997).
Anton D. Hinton–Bayre, "Mild Head Injury and Speed of Information Processing," 19 J. Clin. Exp. Neuropsychology 275 (1997).
Mark R. Lovell et al., "Neuropsychological Assessment of the College Football Player," 13 J. Head Trauma Rehabil. 9 (1998).
Joseph Bleiberg et al., "Future Directions for the Neuropsychological Assessment of Sports Concussino," 13 J. Head Trauma Rehabil. 36 (1998).
Nancy R. Temkin et al., "Detecting Significant Change In Neuropsychological Test Performance," 5 J. Int'l Neuropsychol. Soc. 357 (1999).
Anton D. Hinton–Bayre et al., "Concussion in Contact Sports," 21 J. Clin. Exper. Neuropsychol. 70 (1999).
Robert K. Heaton et al., "Detecting Change," 16 Arch. Clin. Neuropsychol. 75 (2000).
Stephen N. Macciocchi et al., "The Impact of Mild Head Injury Frequency On Neuropsychological Functioning" (publication date unavailable).

* cited by examiner

*Primary Examiner*—Kevin Shaver
*Assistant Examiner*—Michael Astorino
(74) *Attorney, Agent, or Firm*—Mark Pohl, Esq.; Pharmaceutical Patent Law, LLC

(57) ABSTRACT

Apparatus and methods for rapidly diagnosing the presence or absence of the symptoms of neurological pathology caused by physical head trauma (such as occurs in contact sports or automobile collisions), disease (such as occurs in Alzheimer's disease), toxins (substance abuse or environmental toxins) or infection (such as occurs as a side effect of later-stage AIDS infection). These inventions are useful for diagnosing neurological pathology, as well as for monitoring recovery from or maintenance or progression of neurological pathology.

1 Claim, No Drawings

NEUROLOGICAL PATHOLOGY DIAGNOSTIC APPARATUS AND METHODS

BACKGROUND

A portion of the disclosure of this patent document contains material that is subject to copyright protection. The copyright owner has no objection to the facsimile reproduction by any one of the patent document or the patent disclosure, as it appears in the Patent and Trademark Office patent file or records, but otherwise reserves all copyright rights whatsoever.

Computers enjoy wide use in the medical arts. For example, medical database systems for storing and transmitting medical data are known in the art. Medical monitoring systems for monitoring certain known, preexisting medical conditions such as for patients with compromised coronary function or pulmonary function are also known in the art. Lacking in the art is a noninvasive, automated method for diagnosing neurologic cognitive performance and other manifestations of possible neurological pathology.

Published patents include the following:

Stephen J. Brown discloses an online system and method for providing composite entertainment and health information, U.S. Pat. No. 5,951,300. This is an "On-line health education" system. It includes displaying health content and entertainment, where the health content "replaces advertisements." Brown also discloses a multi-player video game for health education, U.S. Pat. No. 5,730,654.

Brown also discloses a method for diagnosis and treatment of psychological and emotional disorders using a microprocessor based video game, U.S. Pat. No. 5,913,310. Disclosed examples include "schizophrenia, depression, hyperactivity, phobias, panic attacks, anxiety, overeating, and other psychological disorders" such as "personality disorders, obsessive-compulsive disorders, hysteria, and paranoia."

Brown also discloses a method for treating medical conditions using a microprocessor based video game, U.S. Pat. No. 5,981,603. That patent discloses a method for treating conditions "associated with the patient's behavior pattern or well being." The patent accordingly claims apparatus directed to the treatment of psychological or emotional conditions. See id. at claim 1.

Brown also discloses a modular microprocessor based health monitoring system, U.S. Pat. No. 5,307,263 and U.S. Pat. No. 5,899,855. That system uses a modem to connect a small handheld microprocessing unit to a central data "clearinghouse," which in turn faxes hard-copy reports to the attending physician.

James S. Burns discloses an inhalation device with a dose timer, an actuator mechanism and patient compliance monitoring means, U.S. Pat. No. 5,284,133.

Michael K. Dempsey et al. discloses a patient monitoring system featuring a multi-port transmitter, U.S. Pat. No. 5,687,734. The patent claims a system comprising, inter alia, a multi-port transmitter and a "signal transmission section . . . for transmitting the processed data as a telemetry signal."

Joel S. Douglas et al. discloses an analyte testing system with test strips, U.S. Pat. No. 5,872,713.

Silvio P. Eberhardt discloses a system and method for storing medical histories, U.S. Pat. No. 5,832,488. The system includes a device for communicating with other computers to retrieve large data records about the individual.

Scott Echerer discloses an interactive audiovisual (video conference) communication system for medical treatment of remotely located patients, U.S. Pat. No. 5,801,755.

Jun Fujimoto discloses a home medical system that "includes equipment measuring the electrocardiogram and other heart conditions of a user," U.S. Pat. No. 5,339,821.

David Goodman discloses a personal health network "comprising a facility . . . for collecting and routing information" which utilizes two-way communication between the patient and the facility, and between the health care provider and the facility. U.S. Pat. No. 5,827,180.

Yasuo Kumagai discloses a medical file and chart system "for integrating and displaying medical data," U.S. Pat. No. 5,812,983.

Richard Levin et al. discloses a system for generating prognosis reports for coronary health management, U.S. Pat. No. 5,724,580. The patent discloses a system of formulating a coronary health report "at a centralized data management center for a patient at a remote location," rather than a system which is able to formulate the report where the patient is.

Patrick Lichter discloses a personal computer card for collecting biological data, U.S. Pat. No. 5,827,179. The patent claims a portable computer card used with an air pressure transducer, see id. at claim 1, or a "biological data receiver," see id. at claim 6. The specification explains that the biological data receiver is a device that "can be adapted to receive biological data from a pulse oximetry sensor" or "from an ECG sensor."

Tom Marlin discloses a system for constructing formulae for processing medical data, U.S. Pat. No. 5,715,451. The patent says that rather than providing a prepared statistical analysis package, Marlin discloses a computer interface to construct statistical and other mathematical formulae to ease the analysis of clinical data.

Stephen Raymond et al. discloses a health monitoring system that "tracks the state of health of a patient and compiles a chronological health history . . . us[ing] a multiparametric monitor which . . . automatically measures and records a plurality of physiological data from sensors in contact with the patient's body." In this system, "[t]he data collected is not specifically related to a particular medical condition" such as neurologic pathology. U.S. Pat. No. 5,778,882.

Norbert Reiner et al. discloses a "care giver data collection and events reminder system for an infant," U.S. Pat. No. 5,691,932.

Mitchell Rohde discloses a portable medical diagnostic device, U.S. Pat. No. 5,876,351. The patent describes the claimed invention as a "portable and modular electrocardiogram (ECG) medical device."

Myron Shabot et al. discloses a system for automatic critical event notification, which "continuously monitors patient statistics and lab data . . . and automatically pages a responsible physician," U.S. Pat. No. 5,942,986.

Michael Swenson et al. discloses a virtual medical instrument for performing medical diagnostic testing, U.S. Pat. No. 5,623,925 and U.S. Pat. No. 5,776,057. The instrument "includes a universal interface having a number of electrical contacts and sets of electrical conduits associated with the different stored diagnostic test protocols. * * * The system is constructed to enable the selected diagnostic test protocol to be performed on a patient after the corresponding set of electrical conduits are connected to the universal interface contacts and to the patient."

Christopher Tacklind et al. discloses a system for monitoring and reporting medical measurements, U.S. Pat. No. 5,549,117 and U.S. Pat. No. 5,626,144 and U.S. Pat. No. 5,704,366 and U.S. Pat. No. 5,732,709.

Paul Tamburini et al. discloses a diagnostic assay for Alzheimer's disease based on the proteolysis of the amyloid precursor protein, U.S. Pat. No. 5,981,208.

Takahiro Yamaura discloses a remote medical system "in which vital signs . . . are transferred to a first local server through a telephone line," United States Pat. No. 5,951,469.

The aforementioned patents disclose medical database systems for storing and transmitting medical data, and medical monitoring systems for monitoring coronary function or pulmonary function. The non-patent literature discloses standards for manually diagnosing concussion, as occur in sports. See generally, American Academy of Neurology, "The Management of Concussion in Sports," *Neurology* v.48, pp. 581–85 (1997); Cantu, R. C., "Minor Head Injuries In Sports," *Adolescent Medicine* v.2, pp. 17–30 (Hanley & Belfus Publ., 1991); Colorado Medical Society, *Guidelines for the Management of Concussion In Sports* (revised) (1991); Jordan, B. D., "Mild Head Injuries In Sports Summit," in *Sports Injuries* (1994).

Not disclosed in the prior art—nor even suggested in it—is a computing apparatus for diagnosing or measuring neurological pathology. There is a need for such an apparatus that is easy to use, portable, and durable, so that it can be used by sports team coaches on the field, by geriatric care nurses in nursing homes or doing home care, by emergency room and long-term care physicians in hospitals, by police and paramedics, and even by patients themselves on their home or hand held computers.

SUMMARY

We have invented a solution which allows for the rapid assay of the existence or absence of, and the quantification of changes over time, of the symptoms of probable neurological pathology. Our invention entails using a computing device to play for a patient a series of cognitive function tests, receiving the patient's test responses, analyzing these responses to form a cognitive performance level for the patient, and forming a conclusion regarding whether symptoms of neurological pathology probably exist or are absent in the patient. Saliently, in contrast to the prior art, which teaches manual, one-time testing, our invention enables the comparison of multiple test results over time, to assess the change over time in a patient's responses. The patient's degree and rate of change over time is, in certain ways, significantly more informative that a static, one-time score.

A version of our invention entails doing this process at least twice—once to establish a "baseline" measure of the patient's normal cognitive performance (e.g., before mechanical concussive trauma), and again at one or more later times (e.g., after trauma). This enables one to assess changes in the patient's cognitive performance.

Another version of our invention entails doing this at least two times after the patient may have incurred cognitive impairment (as by concussion, for example). This version is useful for tracking recovery from neurological pathology (as in traumatic brain injury, for example). In this use, the patient has no "normal" baseline. Rather, the patient's improvement in cognitive functioning is detected over time, after neurologic pathology is incurred. In this use, our invention can determine when a patient stops improving, and therefore when a patient has reached maximum recovery and no longer benefits from medical treatment.

Similarly, our invention can detect that there has been no change from a given baseline result, regardless of whether that baseline is from a healthy or an impaired state. For instance, our invention can help inform that someone probably does or does not have Alzheimer's disease, if their baseline is stable or unstable from year to year. Similarly, if a patient with Multiple Sclerosis has cognitive functioning which is stable over time, our invention provides a useful indicator of the patient's health and prognosis.

DETAILED DESCRIPTION

As used herein, the term "neurological pathology" includes neurological impairment and other kinds of cognitive impairment due to physical (as opposed to solely emotional) causes. Such physical causes are diverse, and include mechanical trauma either external (physical cranial concussion) or internal (stroke, for example), biological trauma (an infection, for example, including meningitis or AIDS), chemical trauma (exposure to environmental toxins, drug or alcohol abuse), preexisting conditions such as attention deficit disorder, and age-related senescence and Alzheimer's disease. In fact, an advantage of our invention is that it is useful regardless of the cause of the neurological pathology—and regardless of whether neurological pathology is known to exist.

The term "neurological pathology testing protocols" is used to connote cognitive testing protocols to measure cognitive functions (immediate and short-term memory and pattern recognition, for example) by providing the patient or user with a series of sensory stimuli, and measuring the user's ability to consciously and voluntarily respond to and remember said stimuli.

To make our invention, one can use any of a wide variety of cognitive function testing protocols. Examples known in the art include psychological tests commercially available from The Psychological Corporation, a division of Harcourt Brace Jovanovich Publishers, New York, N.Y. The specific identity of the protocols is not determinative; our invention works with an extremely wide variety of these testing protocols.

In our preferred embodiment, the neurological pathology testing protocols are visual or auditory. That is to say, they entail visually or auditorially displaying for the user a series of images or sounds, and measuring the user's ability to remember and respond to these. We disclose and discuss the below the specific details of some examples of visual neurological pathology testing protocols.

Our invention is not, however, limited to these specific testing protocols disclosed below. One can readily make our invention using other visual testing protocols. One can even make versions of our invention using other types of sensory response protocols. For example, one can make our invention using auditory stimuli, in place of visual stimuli. This may be necessary for assaying blind or visually-impaired users. This may also be preferred as advantageous to garner a more full picture of the patient's audio, visual, and even tactile responsiveness to cognitive testing protocols.

As used herein, the term "Memory" denotes computer readable memory on tangible media, which is able to store the test protocols, receive user responses, store a response evaluation protocol, and process said user responses according to said response evaluation protocol to generate a result (or "score"). In one version of our invention, the Memory is one single piece of electronic hardware, able to perform all of the required functions.

The Memory need not be one physical unit, however. In one preferred version, the Memory which receives the patient's responses into Memory which is physically located in an Internet-capable wireless phone, while the Memory which stores the most up-to-date version of the neurological pathology testing protocols, and the software to perform the complex user response evaluation, is in Memory physically located in an Internet accessible computer server. One of the advantages of our invention is that one can make it using an extremely wide variety of physical Memory configurations, as long as one provides Memory to perform each of the required functions.

As used herein, the term "computing apparatus" includes personal computer microprocessors for both stand alone computers and those connectable to an external network or software source such as the Internet. The term also includes any electronic hardware which can execute the neurological testing routine herein described.

Thus, for example, our invention can be made using a personal handheld electronic organizer, such as the PALM PILOT III (™), PALM PILOT V (™) or PALM PILOT VII (™), each commercially available from Palm Computing, Inc., Santa Clara, Calif., a WINDOWS CE (™) (Microsoft Corporation, Redmond, Wash.), wireless application protocol standard or blue tooth standard appliance, a wireless telephone with adequate memory, a wireless communications device connectable to an external software source (such as the Internet), or a dedicated medical device whose sole function is to execute the cognitive testing protocols. Our invention can even be made using a television set, where the television is capable of receiving test responses from the subject, via a television remote-control device, for example. This is one of the advantages of our invention—it is extraordinarily flexible, and can be easily produced in an extremely wide variety of hardware. Our invention thus can be made in various versions which are durable, portable, inexpensive, etc . . . , as desired by a given kind of user.

As used herein, the term "Display" denotes apparatus to render the testing protocol perceivable by the user. In our preferred version, the display is the visual display screen on a portable personal computer (or PDA device) or on a wireless telephone. One can use other visual displays, however, including television screens or projector-based systems such as one finds for visual acuity testing at the optometrist's. Further, where one uses non-visual testing protocols, the Display will necessarily entail the ability to display the non-visual information. For example, if one uses sound auditory testing protocols, then the Display will need to include audio speakers or the like.

As used herein, the term "Response Input" denotes apparatus that the test user can use to input their responses to the test protocol into the Memory. In our preferred version, the Response Input is a keyboard or personal computer "mouse." However, one can use the stylus from a hand held computing device, punch pads or a joystick, and so forth, or other types of electronic devices (e.g., wireless telephones, handheld computing devices, touch screen displays) and non-keyboard devices as appropriate. For example, one can use a television infrared remote-control unit, where the Display is a television. The Response Input can be anything able to communicate the user's responses to the Memory.

As used herein, the term "user response analysis software" is software capable of analyzing the user's responses to the neurological pathology testing protocols, to assess whether symptoms of neurological pathology likely exist or are absent in the user, based on the user's responses to the neurological pathology testing protocols. The user response analysis software includes a computer readable data structure on computer readable, tangible media to store both patient's responses, and the statistical analysis protocols that use the patient's responses as variable inputs. Such statistical analysis allows the most information to be obtained from these responses. Used appropriately, the statistical analysis enables the user to draw more sensitive, sophisticated conclusions from the user's responses. Statistical analysis capability had not before been combined in a single system with cognitive-function data (response) gathering capability. We disclose in detail below our preferred version of user response analysis software.

The term "Output" denotes a device capable of outputting the results of the user response analysis software computation. In our preferred embodiment, the Output includes two components: (a) a computer display screen, the same screen used as the "Display" to display the tests to the patient.; and (b) a communications device to communicate the user's test results from the user response analysis software to a Memory for storage and later retrieval. Alternatively, one may use a printer, a modem (including a wireless communication device), a disk drive, or any other combination of hardware appropriate for the given version of our invention. For example, with a blind user, the Output may be an audio speaker.

The term "communication network" includes communication networks both open (such as a ground-line telephone, a radio, or a broadcast television network or the Internet) and closed (such as an intranet or a restricted access local area network).

Neurological Pathology Testing Protocols

In the best mode we currently know of to practice our invention, one uses neurological pathology testing protocols such as the following ones. These specific protocols are protected by copyright, ©2000 Head Minder Inc. and ©2000 Xcape, Inc.

Administration of the testing protocols is preceded by displaying an ethical statement on the privacy of the test results and a legal disclaimer. The testing protocols begin only after the user's identity is verified by a test administrator, or by the user entering a code such as their social security number and a secret password. Before commencing the testing protocols, the user is informed that they should not take the tests if the user has recently used alcohol or other drugs capable of affecting cognitive ability.

Administration of the testing protocols is also preceded by gathering certain general information on the user. This information can be useful or necessary to best administer the tests and interpret the test results. This general information includes the patient's Name, the e-mail and street addresses and telephone numbers for the patient, the patient's physician, the local hospital, and the patient's legal guardian (if applicable), so that any of these can be contacted quickly in an emergency. In our preferred embodiment, the apparatus has a communications device such as wireless telephone capability or a modem. Similarly, we prefer to include contact information for the patient's health insurance provider, so that test information and results can be directly communicated to the insurer without intervening manual data transcription. The patient's date of birth and school grade are, in our preferred embodiment, entered into the software and used to determine which version of certain testing protocols to administer (we prefer to provide certain testing protocols in several different versions, each version suitable for a certain age group).

The Test Date can be entered automatically by the computing device if it has a timer/clock function. The patient's gender, sports played, dominant hand (right, left, ambidextrous), and known prior history of type and date of prior seizures, concussions, reading problems, special education classes, native language, etc . . . , all can be used to adjust or interpret the testing protocol results. A chart of pupil sizes can be included, to allow the patient (or someone else) to quantify the patient's pupil size(s).

If the testing protocol is supervised by someone other than the patient, we prefer to include an electronic "signature" to be entered by the test supervisor, to create a medical record authenticating who supervised the test.

We prefer that the testing protocols themselves be arranged or ordered to put at the very beginning those tests most indicative of the most severe neurologic injury. This enables the software to rapidly triage patients and indicate, for severely impaired patients, that medical intervention may be required immediately, without forcing the patient to complete each and every one of the testing protocols. Similarly, we prefer to order the testing protocols so that patients with superior cognitive function can, if desired, take a longer battery of assays, and obtain a statistically more accurate and precise measure of cognitive function.

At the beginning of the testing protocols, the user is shown the keyboard layout, and shown which keys are needed for responding. For each testing protocol, Screen Instructions are displayed on the Display, and the user must respond appropriately before the protocol begins.

Each cognitive function testing protocol comprises a series of stimuli shown to the user, to which the user must respond. While it is possible to make testing protocols which use words, we prefer at the moment to use protocols which are based on images, not words. This minimizes the data bias based on less than perfect literacy, using a nonnative language for the testing protocols, and the like.

Examples of cognitive function testing protocols include the following visual testing protocols:

Tracking Part I;
Tracking Part II
Incidental Learning Part I;
Incidental Learning Part II;
Matching;
Response Direction Part I;
Response Direction Part II;
Response Inhibition;
Memory Cabinet Learning;
Memory Cabinet Delayed Recall;
Scanning Speed and Accuracy;
Reaction Time;
Cued Reaction Time;
Visual Memory Part I;
Number Sequencing;
Visual Memory Part II; and
Number Recall.

These protocols are examples. Our preferred embodiment uses many different specific test protocols. This makes it less likely that a user will memorize a specific test protocol and the perceived "correct" responses to it.

We now more fully describe each these examples of testing protocols.

Tracking Part I Testing Protocol

At the beginning of this testing protocol, the Display displays the following Screen Instructions:

You are about to see a grid with 9 spaces, just like a tic-tac-toe board. A ball will appear in one of the nine spaces. A moment later, the ball will disappear. The ball will then reappear. If the ball appears in a different space, then do nothing. If the ball reappears in the same space as the immediately preceding time, then press the SPACE BAR. Press the SPACE BAR when you are ready to begin.

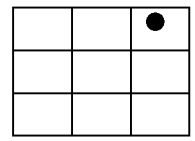

The ball is displayed in a square for 1,500 milliseconds, followed by 500 milliseconds of all blank squares. If the ball appears in the same square two times in a row, the patient should press the space bar. The patient inputs their responses into the Response Input, and thus into the Memory, for further processing by the patient response analysis software. We prefer the testing protocol to present approximately thirty stimuli over about one minute.

Tracking Part II Testing Protocol At the beginning of this-testing protocol, the Display displays the following Screen Instructions:

You are about to see the same grid as before. This time, press the SPACE BAR if the ball appears not in the space immediately preceding, but the space before that one.

The ball is displayed in the square for 1,500 milliseconds, followed by 500 milliseconds of blank squares. If the ball appears in the same square as the time before the previous time, the user should press the space bar. The patient inputs their responses into the Response Input, and thus into the Memory, for further processing by the patient response analysis software. We prefer to display about sixty stimuli over about two minutes. This test may be modified for patients with high cognitive functioning to require a response for the third preceding position, rather than the second or the immediately preceding one.

Incidental Learning Part I

At the beginning of this testing protocol, the Display displays the following Screen Instructions:

Soon you will see a series of pictures appear on the screen. Whenever you see a picture of a plant (such as a fruit, tree or vegetable), press the space bar. If you see a picture of anything else, then do nothing. Try to be fast without making mistakes. You are being timed on how fast you respond. Press the space bar when you are ready to begin.

The Display then displays pictures of plants, animals, and everyday objects. Each picture is displayed for 2 seconds, followed by 1 seconds of blank screen. The patient inputs their responses into the Response Input, and thus into the Memory, for further processing by the patient response analysis software. We prefer to display about forty stimuli (about ten plants, 15 animals and 15 inanimate objects) over about two minutes.

Incidental Learning Part II

At the beginning of this testing protocol, the Display displays the following Screen Instructions:

Soon, you will see a series of pictures. Some are from the series you saw a few minutes ago, while some are new. When you see a picture that you recognize from a few moments ago, press the space bar. If you see a picture that you have not seen before, then do nothing. Try to be fast without making mistakes. You are being timed on how fast you are. Press the space bar when you are ready to begin. The Display then displays pictures of plants, animals and everyday objects. About twenty images from the Incidental Learning Part I are repeated. Each picture is displayed for 2.0 seconds, followed by 1.0 second of blank screen. The patient inputs their responses into the Response Input, and thus into the Memory, for further processing by the patient response analysis software.

In our preferred embodiment, separate statistics for animate and inanimate picture responses are collected and compared. We prefer about forty stimuli over about two minutes. We prefer to give this test after Incidental Learning Part I and another, intervening task.

Matching

At the beginning of this testing protocol, the Display displays the following Screen Instructions:

You are about to see, for ten seconds, ten matching pairs of shapes laid out in a grid. Study the shapes' locations. The shapes will then be hidden under small squares. Once the shapes are hidden, use your mouse to click on any square. The shape hidden beneath the square will appear. Then, use your mouse to click on the square that you think covers the matching shape. If you do not find the matching shape, then both shapes will be covered again. Repeat the process until you find all the matching pairs. Try to make all the matches in as few tries as possible. You will not be timed. Press the space bar when you are ready to begin.

The user must find ten matching pairs of shapes. All pairs are initially displayed for ten seconds, and then covered. In the example above, the Display displays one shapes. The user must then try to find the location of the other. If the user is correct, both shapes in the pair stay uncovered. Otherwise, both will be covered up again. The test continues until all matches are made or until the user attempts forty guesses. There is no time limit. The patient inputs their responses into the Response Input, and thus into the Memory, for further processing by the patient response analysis software.

Response Direction Part I

At the beginning of this testing protocol, the Display displays the following Screen Instructions:

Soon, you will see numbers appear briefly on the screen. Place your left index finger on the 1 key and your right index finger on the 0 key. When you see the number "1" displayed on your screen, press number 1 on your keyboard. When you see the number "0" displayed on your screen, press number 0 on your keyboard. If you see any other number, do nothing. Try to be fast without making mistakes. You are being timed on how fast you respond. Press the spacebar when you are ready to begin.

The Display then displays a number for about 0.5 seconds, followed by 1.5 seconds of blank screen. Responses can occur anytime before the next digit is displayed. The patient inputs their responses into the Response Input, and thus into the Memory, for further processing by the patient response analysis software. We prefer displaying about sixty stimuli over about two minutes.

Response Direction Part II

At the beginning of this testing protocol, the Display displays the following Screen Instructions:

Soon, you will see numbers appear briefly on the screen. Place your left index finger on the 1 key and your right index finger on the 0 key. Do the inverse of what you did on the last test. That is, when you see the number "1" displayed on your screen, press number 0 on your keyboard. When you see the number "0" displayed on your screen, press number 1 on your keyboard. If you see any other number, do nothing. Try to be fast without making mistakes. You are being timed on how fast you respond. Press the spacebar when you are ready to begin.

The Display then displays a number for about 0.5 seconds, followed by 1.5 seconds of blank screen. Responses can occur anytime before the next digit is displayed. The patient inputs their responses into the Response Input, and thus into the Memory, for further processing by the patient response analysis software. We prefer displaying about sixty stimuli over about two minutes.

Response Inhibition

At the beginning of this testing protocol, the Display displays the following Screen Instructions:

Shortly, you will see a series of pictures.

Press the space bar every time you see a picture except if it is of an animal. Press the spacebar as fast as you can. You are being timed. Remember, press the space bar every time you see a picture except if it is an animal. Press the space bar when you are ready to begin.

The Display then displays pictures of objects, plants, and animals. Each picture is displayed for 2.0 seconds, followed by 1.0 seconds of blank screen. The patient inputs their responses into the Response Input, and thus into the Memory, for further processing by the patient response analysis software. We prefer to use about sixty five stimuli over about 3.3 minutes.

Memory Cabinet Learning

At the beginning of this testing protocol, the Display displays the following Screen Instructions:

In a moment, you will see a cabinet with nine common objects placed on different shelves. You will have twenty seconds to memorize where each object is stored. Study hard. Doors will then close to cover the objects and you will be asked to find them, one at a time. You can do this by either (A) pressing the number key (1–9) on your keyboard that is the same as the door where you think the object is hidden, or (B) pointing and clicking your computer's mouse on the door where you think the object is hidden. If you make a mistake, then the test will remind you where the object is, so that you can find it later. You will be asked to find each object a total of four times. Press the space bar when you are ready to begin.

The user must memorize the locations of nine common objects. In one version, we prefer to use toys as the objects. The locations are randomly generated for each user, to minimize users being able to "memorize" the locations. The user is queried about the locations one at a time. The patient inputs their responses into the Response Input, and thus into the Memory, for further processing by the patient response analysis software. After one round (9 queries), there is a second 10-second display, and then the process repeats. This continues until the user has been asked for a location of each object four times. If the user guesses incorrectly, then the correct location is briefly shown. If he guesses correctly, the Display displays "correct." Statistics are collected for each round. There is no time limit.

Memory Cabinet Delayed Recall

At the beginning of this testing protocol, the Display displays the following Screen Instructions:

A few moments ago, you saw a cabinet with nine objects placed on different shelves. In a moment, you will be asked to find those items one at a time, just like you did before. This time, you will not see the objects first, and you will not be told if you are right or wrong. Press the spacebar when you are ready to begin.

There is no initial display of objects. The user must recall their locations from Memory Cabinet Learning. The patient inputs their responses into the Response Input, and thus into the Memory, for further processing by the patient response analysis software. There is only one round of queries, and no feedback about the correctness of a response. This test must be given after Memory Cabinet Learning, and preferably after another intervening task.

Scanning Speed and Accuracy

At the beginning of this testing protocol, the Display displays the following Screen Instructions:

Now, look at the sample shapes below. The shapes are in two groups. If both the shapes on the left hand side of the line are also on the right hand side of the line, press the space bar ONCE. If the shapes are not BOTH on the right hand side, then press the space bar TWICE. You only get one chance for each item. Remember—press ONCE for yes and TWICE for no. Work as fast as you can without making any mistakes. Press the space bar when you are ready to begin.

The Display then displays to the patient two groupings of symbols, one on the left side of the Display and one grouping on the right side of the Display, like this:

¿ Ã § ¶ š ? § ¿ Ã Å Each of approximately thirty groupings of symbols appears separately. The patient inputs their responses into the Response Input, and thus into the Memory, for further processing by the patient response analysis software. We prefer to fix the time required at ninety seconds.

An alternate version of this testing protocol is to ask the patient to hit the number "1" key if one target shape is present on the right side of the Display. and the number "2" key if both target shapes are present there.

Reaction Time

At the beginning of this testing protocol, the Display displays the following Screen Instructions:

Look at the sample white circle below. Each time that you see the white circle, press the space bar.

Try and be quick without making mistakes. Press the space bar when you are ready.

The Display then displays a series of pictures to the patient, using a ratio of 1 "target" image (in this example, a white circle) for every several non-target images (in this example, nonwhite circles) displayed.

The patient inputs their responses into the Response Input, and thus into the Memory, for further processing by the patient response analysis software. In our preferred version, in the Reaction Time testing protocol, the visual stimulus duration is 1.5 seconds, followed by 0.5 seconds of blank screen. The patient's response can therefore occur any time within the 1.5 second stimulus, but is not allowed thereafter.

For the personal computer versions of our inventions (in contrast to, for example, the PALM PILOT (™) based versions), we prefer using certain software operating systems most able to accommodate the rapid response time limits of this testing protocol. Personal computer timers operate independently of the microprocessor speed. Thus, using a 266 MHz microprocessor, or a 450 MHz one, does not affect timer speed. However, different operating systems have different rates of updating the timer. Thus, on WINDOWS 3.11(™), WINDOWS 95(™) and WINDOWS 98(™) (each commercially available from Microsoft Corp., Redmond, Wash.), the timer is updated only 18.2 times per second, resulting in a maximum resolution of ±27 milliseconds. For many testing protocols, this will have no significant impact.

Cued Reaction Time

At the beginning of this testing protocol, the Display displays the following Screen Instructions:

Press the space bar only when the white circle is displayed after a black square is displayed. Do not press the space bar if the white circle is displayed after any other shape, nor any other color of square. Remember, press the space bar only when the white circles is displayed after a black square. Try and be quick without making mistakes. Press the space bar when you are ready to start.

The Display then displays the black square followed by white circle pair, in a ratio of 1:6 with total other stimuli. The ratio of the target (white circle) with target primer (black square), to target without a target primer, is 2:1. The patient inputs their responses into the Response Input, and thus into the Memory, for further processing by the patient response analysis software. This portion of the testing protocol takes 3 minutes.

Visual Memory Part I

At the beginning of this testing protocol, the Display displays the following Screen Instructions:

Now, you will see a series of pictures appear on the display. Sometimes, you will see a picture a second time. Each time you see a picture for the second time, press the space bar. Press the space bar when you are ready to begin.

The Display then displays a series of pictures, as for example:

♣ ↵ X̂ ♣ ♦ Ø ● ≈ ● ≈ Each of the single forty pictures is displayed for two seconds. Of the forty pictures, twenty are repeated and twenty are not, for a test time of two minutes. The patient inputs their responses into the Response Input, and thus into the Memory, for further processing by the patient response analysis software.

Number Sequencing

At the beginning of this testing protocol, the Display displays the following Screen Instructions:

Below is a key that pairs the numbers 1 through 9 with symbols. Beneath the key, you will see a series of symbols with empty boxes underneath. Fill in the correct numbers for each symbol using the numeric keypad. If you make a mistake, just keep going. Try and fill in as many numbers as you can. Press the space bar once to begin.

The Display then displays, for ninety seconds, a screen like this:

| | | KEY | | | |
|---|---|---|---|---|---|
| β | φ | Þ | ‡ | ‰ | << |
| 1 | 2 | 3 | 4 | 5 | 6 |
| | | TEST | | | |
| φ | ‰ | φ | << | Þ | ‡ |
| Þ | φ | ‰ | ‡ | ‰ | φ |

The patient inputs their responses into the Response Input, and thus into the Memory, for further processing by the patient response analysis software. In our preferred embodiment, we use animal silhouettes rather than typographic symbols, but words, numbers, and any other visual indicia are all acceptable.

Visual Memory Part II

At the beginning of this testing protocol, the Display displays the following Screen Instructions:

Just a few moments ago, you saw a list of pictures. Some you saw once, others twice.

Press the space bar when you see a picture that you recognize from before. It can be one that you just saw once, or one that you saw twice. Press the space bar when you are ready to begin.

The Display then displays a series of pictures, one every two seconds. All the forty pictures from the Visual Memory Part II testing protocol are displayed, in addition to twenty new pictures, over a two minute total time. The patient inputs their responses into the Response Input, and thus into the Memory, for further processing by the patient response analysis software.

Number Recall

At the beginning of this testing protocol, the Display displays the following Screen Instructions:

Now, you will see a series of numbers appear on the display, followed by a display screen with some blanks on it. Using the number keys, enter the numbers in the blanks in exactly the same order as you see them. You can use the backspace key to change your answer if you think you have made a mistake. Press the space bar when you are ready to begin.

The Display then displays a series of individual numerals, one numeral at a time, like this:

5 3

Each group of numerals is displayed for 750 milliseconds. The first groups displayed consist of only two numerals. Latter groups consist of longer and longer groups of numerals:

7 4 8 2 9

The patient inputs their responses into the Response Input, and thus into the Memory, for further processing by the patient response analysis software. The testing protocol continues until the patient makes two consecutive errors on the same level of difficulty (i.e., two consecutive errors with numeral groups having the same quantity of numerals in them). When the patient makes these two consecutive errors, the testing protocol stops.

Number Sequencing

At the beginning of this testing protocol, the Display displays the following Screen Instructions:

Now, you will see a group of numerals appear on the display, followed by a display screen with some blanks on it. Using the numeric keypad, enter the numbers in the blanks in ASCENDING order. That is, order them from lowest to highest. You can use the backspace key to change your answer if you think you have made a mistake. Press the space bar when you are ready to begin.

The Display then displays a group of numbers, like this:

5 3 4

The patient inputs their response (the correct response would be "3 4 5" in the immediate example) into the Memory. Each group of numbers is presented for two seconds. The first groups displayed consist of only three numerals. Latter groups consist of longer and longer groups of numerals:

2 8 3 1 9

The patient inputs their responses into the Response Input, and thus into the Memory, for further processing by the patient response analysis software. The testing protocol is discontinued when the patient makes two consecutive errors on the same level of difficulty (i.e., with two consecutive number groups having the same quantity of numbers in them). This test portion takes approximately three minutes.

Summary

On completion of the testing protocol(s), the patient is informed that the testing is complete. Either after completion of all protocols, or during the test process, the patient's response data is used as variable inputs in the patient response analysis software.

Patient Response Analysis Software

The user's results for the neurological pathology testing protocols are then analyzed statistically, to obtain the most information from them. In our invention, the statistical analysis capability is integrated into the system. This is done by incorporating directly into our system, patient response analysis software. The patient response analysis software uses as variable inputs the testing protocol results discussed above. The patient response analysis software then statistically analyzes these responses and calculates certain values for each specific testing protocol, the values for certain protocols combined, and the values for all the protocols combined. We discuss each in turn.

In our preferred version, we use the following statistical analysis protocols. This compilation of these statistical protocols is protected by copyright, ®1999 Xcape, Inc.

Individual Testing Protocols

For each separate neurological pathology testing protocol, the patient response analysis software calculates:

t=Average Response Time y=correct responses

O=Errors of Omission (misses or errors)

C=Errors of Commission (false positives, if applicable)

From these, the following ratios can be derived:

Proficiency Index=(O+C)/t

Discriminability=100×[1−(O+C/Number of Stimuli)] (Note that in our preferred embodiment, neither Proficiency Index nor Discriminability are actually used: we disclose them herein simply to assure the completeness of our disclosure).

Response Bias=(C−O)/(C+O); if no errors then=0.

Response Variability=mean standard deviation of response times.

Response Variability is calculated for the continuous performance test protocol(s) (e.g., the "Tracking" testing protocols, above) only.

Q Level=y−C−O

Retention Index=100×Delayed Recall/Immediate Recall. Retention Index is calculated for the memory tests only.

Test—Retest Correlation

If baseline data is available (either from a patient pool, or specifically from a prior test administered to that patient), then the patient response analysis software can also calculate, for each of the above values, the correlation between a given baseline test value ("a") and the value obtained in a subsequent test ("b"). We denote this correlation here as "r(ab)."

r(ab)=S(ab)/sqrt [S(aa)×S(bb)]

S=Sigma=standard deviation

Mu=mean $S(aa)=SUM [(a-mean (a))^2]$ $S(bb)=SUM [(b-mean (b))^2]$

S(ab)=SUM [abs[(a−mean(a))×(b−mean (b))]]

Selectively Combined Testing Protocol Analysis

In addition to analyzing data for each testing protocol separately, the patient response analysis software combines the results of certain testing protocols for certain analyses.

General Attention=total correct responses for Number Sequencing and Number Recall protocols.

Attention Consistency=the weighted number of digits in Number Sequencing and Number Recall.

Attention Accuracy=(Discriminability for Response Speed+Discriminability for Response Cueing and Inhibition)/2.

Attention Efficiency=(Proficiency for Response Speed+Proficiency for Response Cueing and Inhibition)/2.

Processing Speed Accuracy=(Q Level for Symbol Scanning+Q Level for Number Sequencing)/2.

Processing Speed Efficiency=(Proficiency for Symbol Scanning+Proficiency for Number Sequencing)/2.

Memory Accuracy=(y for Visual Memory Part I+y for Visual Memory Part II)/2.

Memory Efficiency=(Proficiency for Visual Memory Part I+Proficiency for Visual Memory Part II)/2.

Reaction Time Index=average reaction time for Response Speed+average reaction time for Response Cueing and Inhibition. Processing Speed Index=average reaction time for Symbol Scanning+average reaction time for Number Sequencing.

Complex Reaction Time=average reaction time for Visual Memory Part II+average reaction time for Response Cueing and Inhibition.

Total Combined Testing Protocol Values

For all neurological pathology testing protocols combined, the patient response analysis software calculates:

Overall Speed

Overall Accuracy

Overall Proficiency=Overall Speed/Overall Accuracy

In our preferred embodiment, the speed, accuracy and efficiency result indices are generated at the domain level; that is to say, if one neurological pathology testing protocol at baseline is outside the normal range, the software can still generate a statistically meaningful score. If this is not done, then if a patient does not understand the instructions, or has attention deficit disorder, or is disturbed by a telephone call during the test, then that patient's erroneous results will create systematic error which can distort the general score.

Reliable Change Index

The patient response analysis software then calculates a "reliable change index." The reliable change index or other reliable change techniques maybe used to describe the change from the baseline value, which change is statistically reliable. There are many ways known in the art to calculate a meaningful to infer a neurological pathology change index. We prefer to calculate the reliable change index (or "RCI") as follows:

RCI=X(b)−X(a)/s(d)

X(a)=the baseline value

X(b)=the immediate value s(d)=the standard difference for the sub test calculation, as calculated above.

p=the probability of error

Regardless of the specific statistical method used to calculate the RCI, the RCI threshold values should, optimally, be set considering generally accepted statistical principles. One tailed and other statistical tests are possible. In our preferred version, the positive and negative RCI threshold values are derived from accepted medical neurology standards. Examples of accepted medical neurology standards are available in Hinton-Bayre, A. D., et al., "Concussion In Contact Sports: Reliable Change Indices of Impairment and Recovery, " *Journal of Clinical and Experimental Neuropsychology*, v.21, pp. 70–86 (1999). Other values may, however, be used.

For a one tailed test, we prefer to use a negative RCI threshold value of −1.65, with p<0.05. We similarly prefer to use a positive RCI threshold value of −1.04 with p<0.15. Using these amounts, a test result with an RCI≧*31* 1.65, indicates symptoms of neurological pathology likely exist in the patient. By contrast, an RCI≧−1.04, indicates symptoms of neurological pathology likely do not exist in the patient. Other threshold values may, of course, be used.

If an RCI value falls outside its negative RCI threshold range, or if there is at least one active trauma symptom in the pre-testing protocol user survey (e.g., if the user has loss of consciousness, nausea, etc . . . ), then the user response analysis software indicates that symptoms of neurological pathology likely exist in the user. Conversely, if all RCI values are within the positive RCI threshold ranges and if there is no active trauma symptom, then the user response analysis software indicates that symptoms of neurological pathology likely do not exist in the user. If at least one RCI value falls inside the negative RCI threshold range but outside the positive RCI threshold range, and if there is no active trauma symptom, then the user response analysis software indicates that symptoms of neurological pathology may exist in the user.

We prefer that for certain uses (concussion, for example), the patient take the test at least once immediately after concussion occurs, and again after perhaps a half hour wait. This way, the patient's changes over the period immediately post-trauma can be assessed.

For certain applications (contact sports, for example), players can establish a "baseline" score before the season begins, or before physical concussion occurs, and use this baseline to compare to later scores. In such a use, RCI scores which fall too far outside the normal range (we prefer less than two standard deviations from the mean) are rejected, as physical concussion, even severe, may not statistically lower a score which is already quite low. Thus, we prefer to not have such users (nor their physicians) rely on these scores to allow a user to return to athletic play after a potentially severe physical concussion. Low baseline scores could be due to a number of factors including a history of learning problems, distraction and confusion over the instructions or a conscious attempt to fake a lowered score in order to manipulate future test results.

SUMMARY

Although the present invention has been described in considerable detail with reference to certain preferred versions, other versions are possible. Therefore, the spirit and scope of the appended claims should not be limited to only the description of our preferred versions contained in the foregoing discussion. The features disclosed in this specification, and the accompanying claims and abstract, may be replaced by alternative features serving the same equivalent or similar purpose, unless expressly stated otherwise. Thus, unless expressly stated otherwise, each feature disclosed is one example only cf a generic series of equivalent or similar features.

As used in the claims appended, the word "a" includes the singular as well as the plural. The phrase "in communication with" entails both direct communication and indirect communication via one or more intermediary pieces.

We claim:

1. A method of measuring the cognitive performance of an individual comprising:
    a. the individual completing at least one cognitive test with at least one testing protocol;
    b. storing results of said at least one cognitive test in a computer readable media; and
    c. applying a reliable change technique to obtain a statistically meaningful inference of a neurological pathology, wherein the reliable change technique uses at least one baseline of the individual.

* * * * *